United States Patent [19]
Baldecchi

[11] Patent Number: 5,624,378
[45] Date of Patent: Apr. 29, 1997

[54] PUMPLESS VACUUM GENERATION FOR AUGMENTING MALE POTENCY

[75] Inventor: Albert S. Baldecchi, Woodland Hills, Calif.

[73] Assignee: Osbon Medical Systems, Inc., Augusta, Ga.

[21] Appl. No.: 299,289

[22] Filed: Aug. 31, 1994

(Under 37 CFR 1.47)

[51] Int. Cl.$^6$ ........................................ A61F 5/00
[52] U.S. Cl. ................................. 600/38; 600/41
[58] Field of Search ............... 600/38–41; 601/6, 601/9–11

[56] References Cited

U.S. PATENT DOCUMENTS

| | | |
|---|---|---|
| D. 317,504 | 6/1991 | Osbon . |
| D. 317,505 | 6/1991 | Osbon . |
| D. 330,081 | 10/1992 | Walsh . |
| D. 343,454 | 1/1994 | Osbon . |
| D. 343,455 | 1/1994 | Osbon . |
| 1,117,618 | 11/1914 | Ach . |
| 1,225,341 | 5/1917 | Lederer . |
| 2,874,698 | 2/1959 | Sell . |
| 3,421,504 | 1/1969 | Gibbons . |
| 3,631,853 | 1/1972 | Burdette, Jr. . |
| 3,744,486 | 7/1973 | Wilson . |
| 3,820,533 | 6/1974 | Jones . |
| 3,910,262 | 10/1975 | Stoughton . |
| 4,175,554 | 11/1979 | Gerow . |
| 4,210,253 | 7/1980 | Rosler . |
| 4,378,008 | 3/1983 | Osbon, Jr. . |
| 4,641,638 | 2/1987 | Perry . |
| 4,690,135 | 9/1987 | Gerow . |
| 4,718,411 | 1/1988 | Stewart . |
| 4,741,329 | 5/1988 | Marcune . |
| 4,753,227 | 6/1988 | Yanuck, Jr. . |
| 4,856,498 | 8/1989 | Osbon . |

(List continued on next page.)

FOREIGN PATENT DOCUMENTS

| | | |
|---|---|---|
| 148586A1 | 7/1985 | European Pat. Off. . |
| 313836 | 1/1934 | Italy . |

OTHER PUBLICATIONS

Marmar, et al.; Penile Plethsmography On Impotent Men Using Vacuum Constictor Devices; pp. 198–203; Sep. 1988; Urology vol. XXXII, No. 3.

*Primary Examiner*—Angela D. Sykes
*Assistant Examiner*—Samuel Gilbert
*Attorney, Agent, or Firm*—Dority & Manning, P.A.

[57] ABSTRACT

A vacuum chamber is provided with a drive region having outside diameter threads and a longitudinal guide slot. An annular collar carries inside diameter threads for mating with the vacuum chamber threads such that the collar is longitudinally moved relative to the vacuum chamber by user rotation of such annular collar. Coupling members project through the vacuum chamber longitudinal slot from the annular collar to a drivable piston movably received in the vacuum chamber such that controlled movement of such piston at least partially displaces air within the vacuum chamber so as to generate a corresponding level of vacuum in such vacuum chamber. Once a user's male sex organ is placed into the vacuum chamber via an open end thereof, the user may rotate the annular collar so as to displace air within the vacuum chamber and produce a desired vacuum engorgement of the user's male sex organ. The engorged condition may be captured utilizing a cincture band or similar, and thereafter the negative pressure within the vacuum chamber may be released through operation of a valve associated with a closed end of the drivable piston. A vacuum limiter may actuate such valve at a predetermined vacuum level to prevent excessive vacuum chamber negative pressure, for the user's safety and comfort. A pumpless system and methodology results from utilizing the principle of air displacement for generating the vacuum (i.e., negative pressure) within the vacuum chamber.

24 Claims, 5 Drawing Sheets

U.S. PATENT DOCUMENTS

| | | |
|---|---|---|
| 4,856,499 | 8/1989 | Kelly . |
| 5,020,522 | 6/1991 | Stewart . |
| 5,083,556 | 1/1992 | Osbon et al. . |
| 5,095,895 | 3/1992 | Walsh . |
| 5,115,800 | 5/1992 | Matejevic et al. . |
| 5,195,943 | 3/1993 | Chaney . |
| 5,213,563 | 5/1993 | Cox . |
| 5,234,402 | 8/1993 | Osbon . |
| 5,244,453 | 9/1993 | Osbon et al. . |
| 5,306,227 | 4/1994 | Osbon et al. . |

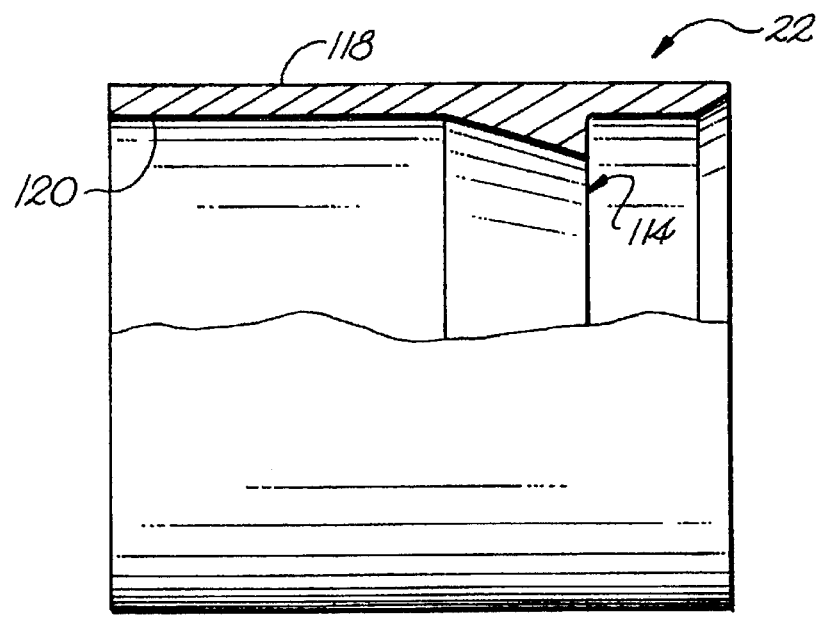
Fig. 11
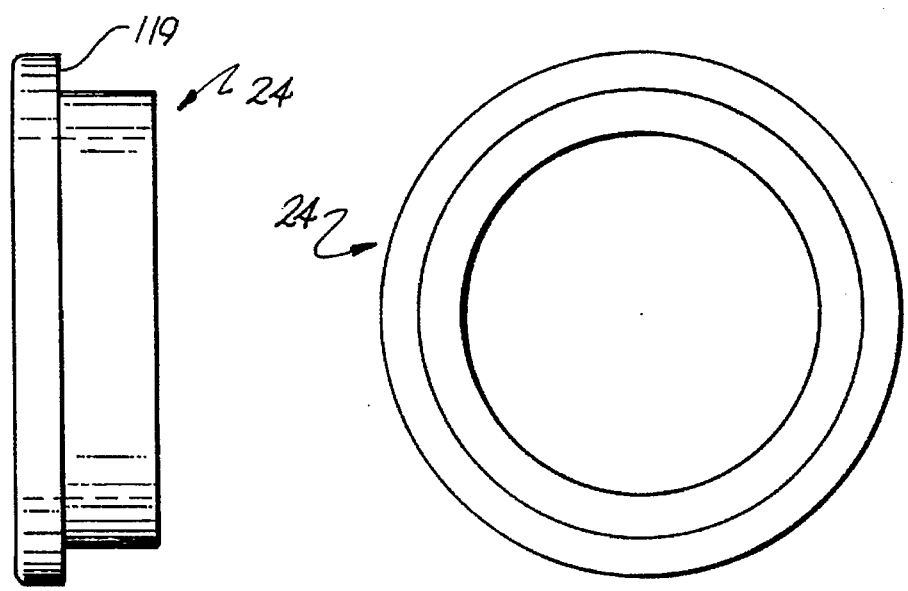
Fig. 13
Fig. 12

PUMPLESS VACUUM GENERATION FOR AUGMENTING MALE POTENCY

BACKGROUND OF THE INVENTION

The present invention relates in general to improved apparatus and methodology for augmenting male potency and in particular concerns related apparatus and methodology utilizing a rotating mechanism for advancing a piston in a vacuum chamber to make use of air displacement in a pumpless arrangement for producing vacuum engorgement of the male sex organ.

The occurrence of male impotence (i.e., the inability to gain an adequate penile erection for coitus) is widely known and the subject of considerable medical and scientific activity. Both surgical and nonsurgical therapies have been available for treatment of male impotence. Vacuum tumescence is one previously known therapy which makes use of a vacuum chamber for producing the desired penile engorgement and rigidity. Such device operates by applying a vacuum force to the penis, which draws blood into the various erectile bodies of the user's male sex organ, i.e., the penis. Such engorgement is produced while the subject's penis is placed within a vacuum chamber or cylinder. Typically, the desired engorged condition is subsequently secured with an elastic or similar material cincture band or the like.

The following United States patents all disclose various examples of vacuum chambers for use in conducting such vacuum erection enhancement therapy.

| PATENT NO. | INVENTOR(S) | ISSUE DATE |
| --- | --- | --- |
| 4,378,008 | OSBON | 3/29/83 |
| 4,856,498 | OSBON | 8/15/89 |
| 5,083,556 | OSBON et al. | 1/28/92 |
| 5,244,453 | OSBON et al. | 9/14/93 |
| 5,306,227 | OSBON et al. | 4/26/94 |

In addition, each of the foregoing patents illustrate examples of elastic bands or cincture rings for securing an engorged condition. Additional prior patents illustrate a variety of such devices, as follows:

| PATENT NO. | INVENTOR(S) | ISSUE DATE |
| --- | --- | --- |
| Des. 317,504 | OSBON | 6/11/91 |
| Des. 317,505 | OSBON | 6/11/91 |
| 5,234,402 | OSBON | 8/10/93 |
| Des. 343,454 | OSBON | 1/18/94 |
| Des. 343,455 | OSBON | 1/18/94 |

One of the problematic areas of vacuum enhancement therapy is the widely varying subjective needs and objective needs and abilities of different patients. Subjective patient needs relate to a number of factors, including, for example, psychological acceptance of the therapy and patient preference among different techniques or approaches. Objective patient needs likewise involve numerous factors, including the physiologic make-up of the user's sex organs, as well as the physical abilities of the patient in areas of agility, strength, and dexterity (all of which can impact selection and use of various systems).

The above exemplary systems, while satisfactory in numerous instances, may nonetheless prove to be less desirable by specific patients for either subjective or objective reasons. The disclosures of all of the above-referenced patents (both utility and design patents) are fully incorporated herein by present reference thereto.

SUMMARY OF THE INVENTION

The present invention recognizes and addresses various of the above-referenced patient needs, both subjective and objective, concerning vacuum erection enhancement therapies. Thus, broadly speaking, a principal object of the present invention is to provide improved vacuum therapy systems and methodology. More particularly, a main concern is providing improved and/or alternative vacuum generating apparatus and corresponding methodology.

It is another more particular object of the present invention to provide improved vacuum generating apparatus for augmenting male potency, and corresponding methodologies, particularly making use of principles of air displacement. In such context, it is yet another more particular present object to provide such an improved apparatus and methodology which further facilitate practice of vacuum erection enhancement therapy.

Still a further present broad object is to provide improved apparatus and methodology which provide further alternatives to patients having preferences and/or physical needs which render use of prior systems and methodologies inconvenient and/or impractical.

It is another more particular object to provide apparatus and methodology which provides an integrated system with few external components. In such context, it is an object to provide such system and methodology which facilitate and enhance the selective control of the user to establish the level of vacuum with a hand operated system. More specifically, it is a present object to provide a rotatable drive arrangement which permits a user to selectively control the level of generated vacuum (i.e., negative pressure) on the user's male sex organ by rotatably positioning a portion of the apparatus relative to the vacuum chamber.

In keeping with the foregoing, it is a present object to provide a further improved system which is still also simple to operate and to understand, thereby improving the psychological acceptance thereof by the patient and lowering patient cost relative to more complicated systems.

Another more particular object is to provide such improved apparatus usable with the practice of subsequently securing an engorged condition with a resilient penile cincture band or similar device, and which apparatus is also amenable to use with extensions, inserts, and other variations within the general technique of vacuum erection enhancement therapy.

Additional objects and advantages of the invention are set forth in, or will be apparent to those of ordinary skill in the art from, the detailed description which follows. Also, it should be further appreciated that modifications and variations to the specifically illustrated and discussed features, steps, or materials hereof may be practiced in various embodiments and uses of this invention without departing from the spirit and scope thereof, by virtue of present reference thereto. Such variations may include, but are not limited to, substitution of equivalent means and features, steps, or materials for those shown or discussed, and the functional or positional reversal of various parts, steps, features or the like.

It is to be further understood that different embodiments, as well as different presently preferred embodiments, of this invention may include various combinations or configurations of presently disclosed features, elements, steps, or their equivalents (including combinations of features or steps or configurations thereof not expressly shown in the figures or stated in the detailed description). One exemplary such embodiment of the present invention relates to an improved vacuum generating apparatus for augmenting male potency. Such present apparatus may include a vacuum chamber for receiving a user's male sex organ, a drivable piston, and rotatable drive means.

Preferably, the foregoing drivable piston is movably received in the vacuum chamber such that controlled movement thereof away from a user's torso at least partially displaces air within the vacuum chamber so as to generate a corresponding level of vacuum in the vacuum chamber. The rotatable drive means is preferably responsive to user selected rotation thereof for controllably moving the drivable piston. With such an arrangement, the user controls the level of resulting vacuum applied with the apparatus to the user's male sex organ.

It is to be understood by those of ordinary skill that reference throughout the subject application to various actuations or manipulations by the "user" can, and do, fully reference and include the patient and any person, partner, or the like assisting the patient to whom the vacuum erection enhancement therapy is being applied with the subject invention.

Another present exemplary embodiment concerns an improved vacuum generating system for therapeutically producing vacuum engorgement of a user's penis. Such system preferably comprises a vacuum chamber, a piston, seal means, rotatable drive collar means, drive coupling means, and vacuum release means.

In such foregoing exemplary embodiment, the vacuum chamber preferably comprises an elongated, generally cylindrical configuration of sufficient size to cover a user's penis. Furthermore, such chamber includes an opening in at least one longitudinal end thereof for receiving the user's penis with the at least one end of such chamber pressed against the user's lower torso. The chamber also further includes outside diameter male threads formed in a drive region thereof and accompanied by a generally longitudinal guide slot in such drive region.

The foregoing exemplary piston includes at least one closed end movably received in the vacuum chamber. The seal means is operative therewith for permitting air displacement within the vacuum chamber whenever the piston is moved away from a user's torso with the vacuum chamber at least one end pressed against the user's lower torso with the user's penis received within the vacuum chamber.

The rotatable drive collar means are preferably generally received about the vacuum chamber drive region and are user rotatable relative thereto. Such collar means have inside diameter female threads formed therein for user controlled threaded operative interaction with the vacuum chamber outside diameter male threads. With such an arrangement, the collar means are selectively positioned along the vacuum chamber drive region by user selected rotation of the collar means relative to the vacuum chamber drive region.

The above exemplary drive coupling means are associated with the vacuum chamber drive region generally longitudinal guide slot and operatively interconnect the rotatable drive collar means with the piston such that the user selected positioning of the collar means establishes corresponding movement and positioning of the piston relative to the vacuum chamber. By such arrangement, a user selectively controls vacuum engorgement of the user's penis received in the vacuum chamber by selectively rotating the rotatable drive collar means.

Lastly, the foregoing exemplary vacuum release means is subject to user actuation for controllably admitting air into the vacuum chamber so as to release vacuum, i.e., negative pressure therein for withdrawal of the user's penis from such vacuum chamber.

The present invention likewise concerns exemplary corresponding methodologies, both concerning the apparatus referenced above and as further discussed in the remainder of this specification.

Those of ordinary skill in the art will better appreciate the features and aspects of such embodiments, methods, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which:

FIG. 11 is a generally side elevational view (with partial cutaway) of an exemplary extension element usable in accordance with the subject invention;

FIG. 12 is an end elevational view of an exemplary insert usable in accordance with the subject invention; and FIG. 13 is a side elevational view of the exemplary insert of present FIG. 12.

Figure 1:
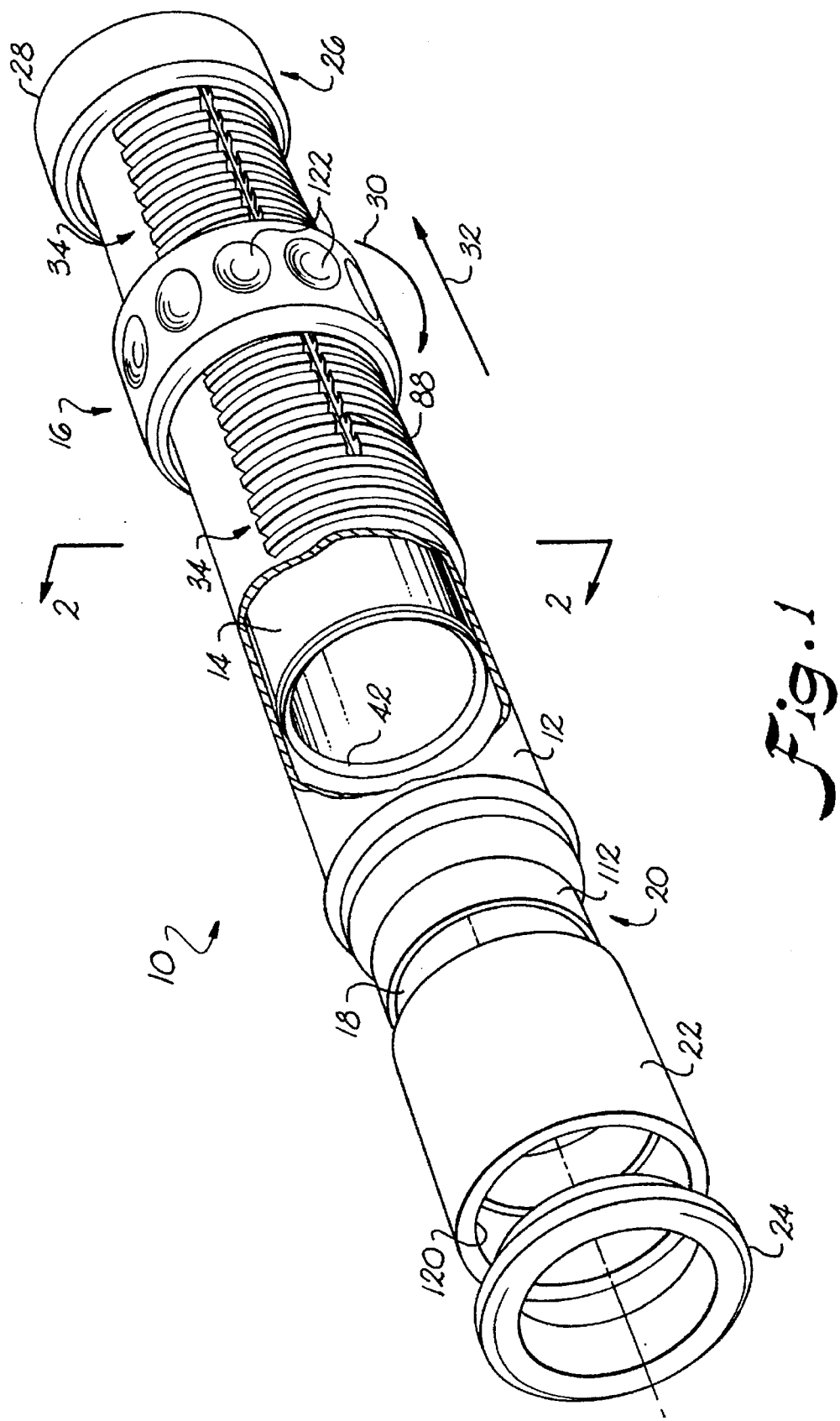
FIG. 1 is a perspective view of an exemplary embodiment of the present invention illustrated in partial cutaway and with partial exploded view of certain alternative (or optional) elements.

Repeat use of reference characters throughout the present specification and appended drawings is intended to represent same or analogous features, elements, or steps of the invention.

DETAILED DESCRIPTION OF THE PREFERRED EMBODIMENTS

FIG. 1 is a generally perspective view of an exemplary apparatus 10 in accordance with the subject invention. Such improved vacuum generating apparatus 10 for augmenting male potency includes a vacuum chamber generally 12 (shown in partial cutaway), a drivable piston generally 14 (only partially seen in FIG. 1) movably received within vacuum chamber 12, and rotatable drive means generally 16. In such arrangement, those of ordinary skill in the art will understand that a user's male sex organ or penis is received within vacuum chamber 12 via an opening generally 18 formed in at least one longitudinal end generally 20 of chamber 12. Drivable piston 14 is also movably received within chamber 12 such that controlled movement of piston 14 away from a user's torso at least partially displaces air within vacuum chamber 12 so as to generate a corresponding level of vacuum (i.e., negative pressure) therein.

In accordance with the subject invention, rotatable drive means generally 16 are responsive to user selected rotation thereof for controllably moving such drivable piston 14. With such an arrangement, the user controls the level of resulting vacuum applied with apparatus 10 to the user's male sex organ.

As further represented by present FIG. 1, the longitudinal end generally 20 of chamber 12 defining opening 18 may alternatively and optionally be provided with an extension insert 22 (see FIG. 11 and its related discussion) and/or a rubberized or similar cushion insert 24 (see generally FIGS. 12 and 13 and related discussion thereof). At the opposite longitudinal end generally 26 of chamber 12, a removable end cap 28 may be provided both for aesthetics and functionality in that the existence of a cover over end 26 substantially prevents undesired entry of materials or substances into chamber 12. End cap 28 also functions to restrict the movement of rotatable drive means 16. However, it will be understood by those of ordinary skill in the art from the totality of the disclosure herewith that generally no negative pressure is established within vacuum chamber 12 between such end 26 and movable piston 14.

In accordance with present methodology, clockwise rotation of rotatable drive means 16 generally in the direction of arrow 30 causes reactive movement of such rotatable drive means along the longitudinal axis of chamber 12 generally in the direction of arrow 32. It will be understood that reverse rotation of rotatable drive means 16 would cause longitudinal movement thereof opposite to the direction of arrow 32. As further discussed herein, rotatable drive means 16 preferably includes internal threading which operatively mates and functions with threading generally 34 preferably received externally on chamber 12.

Figure 2:
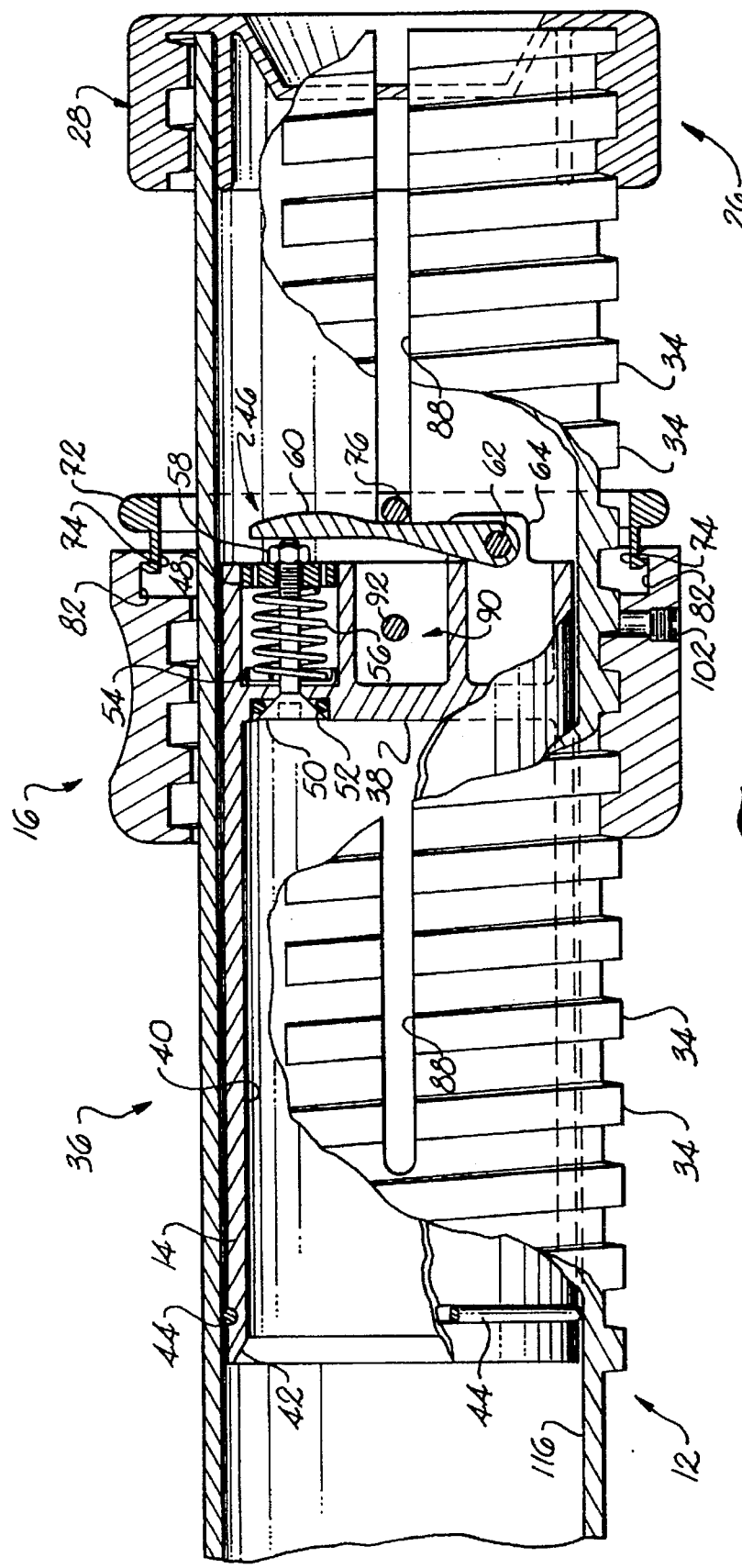
FIG. 2 is an enlarged, partial cross-sectional view of the exemplary embodiment represented in FIG. 1, taken along the sectional line 2—2 indicated therein, particularly referencing a defined drive region of a subject exemplary vacuum chamber.
Figure 3:
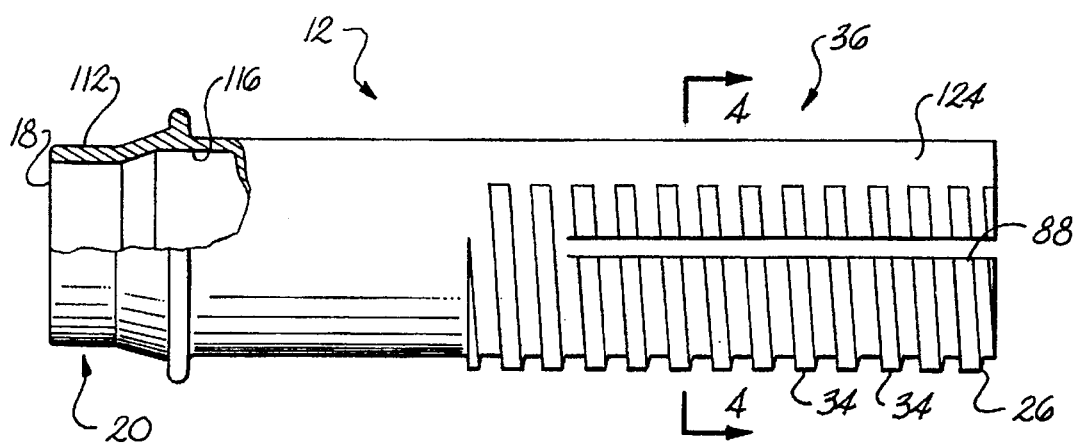
FIG. 3 is a side elevational view (with partial cutaway) of an exemplary vacuum chamber in accordance with the subject invention.
Figure 4:
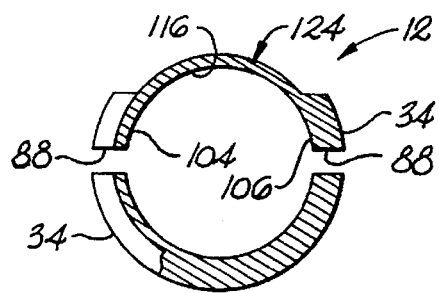
FIG. 4 is a cross-sectional view of the vacuum chamber embodiment of FIG. 3, taken along the sectional line 4—4 indicated therein.

FIG. 2 illustrates an enlarged cross-sectional view of a defined drive region generally 36 of chamber 12, taken along the sectional line 2—2 of present FIG. 1. Such drive region 36 generally corresponds with (i.e., is defined by) the longitudinal region or area of chamber 12 which is accompanied by the outside diameter male threads 34 thereof. FIG. 2 also represents by virtue of partial surface and partial cross-sectional viewing, additional features of the subject invention involving the piston generally 14. FIG. 3 illustrates a generally side elevational view of chamber 12, with partial cutaway, while FIG. 4 illustrates a cross-sectional view of such chamber 12, taken along the sectional line 4—4 indicated in such FIG. 3.

As variously shown in the figures, vacuum chamber 12 for receiving a user's male sex organ is generally cylindrical and sufficiently sized for covering a user's penis. Piston 14 is also generally cylindrical with a relatively smaller diameter than that of vacuum chamber 12 so as to be received therein. Piston 14 generally includes at least one closed end 38 thereof such that movement of piston 14 in vacuum chamber 12 relatively sweeps air therethrough for air displacement. In other words, air is moved away from end generally 20 of vacuum chamber 12 as piston 14 is moved in the direction of arrow 32 by actuation of rotatable drive means 16.

As further represented, piston 14 generally includes a hollow tubular portion 40 for at least partially projecting around a user's male sex organ received within vacuum chamber 12. For such purpose, an opening generally 42 is also provided within hollow tubular portion 40 of piston 14.

As further represented in present FIG. 2, seal means are provided for being operative with piston 14 for permitting air displacement within vacuum chamber 12 whenever piston 14 is moved away from a user's torso while end 18 of vacuum chamber 12 is pressed against the user's lower torso with the user's penis received within vacuum chamber 12. Such seal means preferably includes an O-ring seal generally 44 situated between piston 14 hollow tubular portion 40 and vacuum chamber 12. With such an arrangement, O-ring seal 44 may for example be carried adjacent to the open end 42 of piston sleeve 40, or it may alternatively be carried within an annular channel of chamber 12. In either case, a relatively airtight seal sufficient for present air displacement purposes is maintained while piston 14 moves, at least so long as the travel of tubular portion 40 overlaps with O-ring 44. With such an arrangement, movement of piston end 38 in the appropriate direction results in air displacement for generating negative pressure (i.e., vacuum) within chamber 12, which under proper conditions may have vacuum engorgement effects on the user's penis, as well understood by those of ordinary skill in the art.

Figures 5, 6:
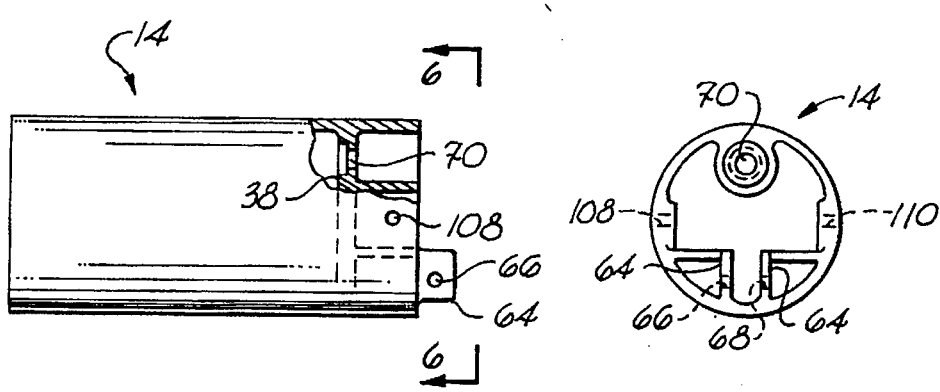
FIG. 5 is a side elevational view (with partial cutaway) of an exemplary piston in accordance with the subject invention.
FIG. 6 is an end elevational view of the exemplary piston of present FIG. 5, taken along the view line 6—6 indicated therein.

As further represented particularly by present FIG. 2, vacuum release means generally 46 may be provided in accordance with the subject invention for regulating the release of vacuum from vacuum chamber 12. Such vacuum release means generally 46, includes an actuatable vacuum pressure release valve generally 48 seated in the piston closed end 38 so as to permit the selected release of vacuum therethrough. More specifically, a screw cap 50 may be seated against a negative pressure valve O-ring 52. A washer 54 comprising a spring seat receives a spring 56, which in turn is axially captured by valve element 48. A nut locking nylon insert 58 or the like may be received on screw 50, such that movement of negative pressure release arm 60 permits the release of vacuum through operation of vacuum release means generally 46. Negative pressure release arm 60 is in turn pivoted about a fixed axis 62, which is mounted on projecting ear 64 formed as part of the closed end 38 of piston 14. FIGS. 5 and 6 respectively represent side and end elevational views generally of piston 14. As shown, projecting ear 64 has two separate members providing openings 66 and 68 through which the fixed point pivoting pin or axis 62 may be received. An opening generally 70 is otherwise operative with vacuum release means 46 for permitting selected release of vacuum from vacuum chamber 12, by user selected admitting of return air to such vacuum chamber interior.

Figures 7, 8:
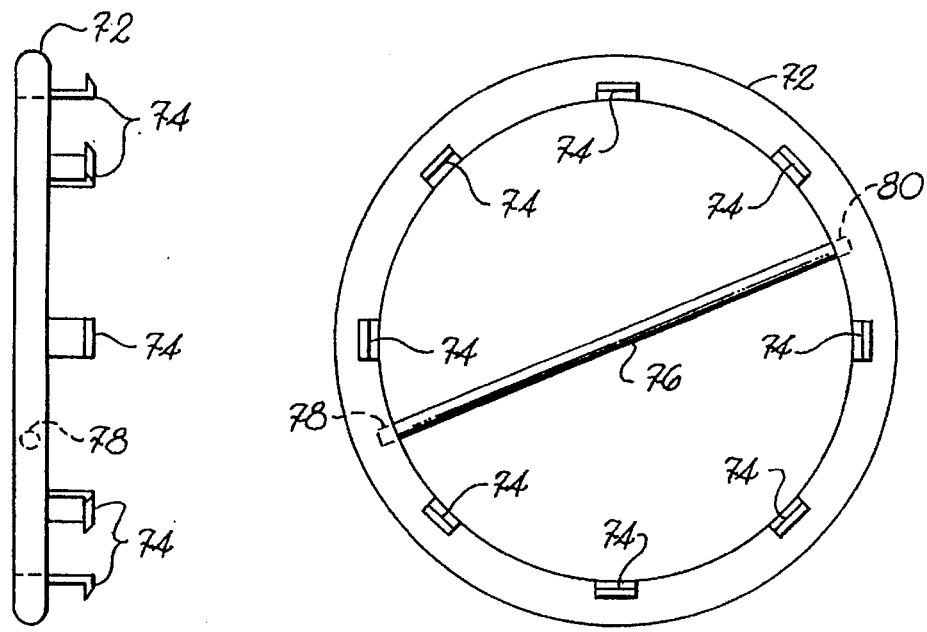
FIG. 7 is a side elevational view of a portion of actuation elements for the control of releasing vacuum from the vacuum chamber in accordance with the subject invention.
FIG. 8 is an end elevational view of the exemplary actuation elements of present FIG. 7.

FIG. 2 in particular further represents a negative pressure release ring 72, which is mountable on rotatable drive means generally 16 through use of a plurality of extending engaging members or tabs 74. Side and end elevational views of such negative pressure release ring 72 are further shown by present FIGS. 7 and 8, respectively. As further represented, an actuating pin or element 76 is received in openings 78 and 80 of ring 72 so as to be carried thereby. By the attachment of ring 72 with plural elements 74 to rotatable drive means generally 16, actuation pin 76 is situated immediately adjacent negative pressure release arm 60. With the travel distance afforded projecting members 74 by the axial width of annular channel generally 82 formed in rotatable drive means 16, a user is able to manipulate ring 72 towards end 18 of vacuum chamber 12 so as to cause actuation of vacuum release means 46 (by pin 76 against arm 60) for selectively releasing a portion of the vacuum within chamber 12, as will be readily understood by those of ordinary skill in the art from the above description and from the figure illustrations themselves.

It will also be readily understood by those of ordinary skill in the art that appropriate selection of the relative strength of spring 56 results in vacuum release means 46 having a vacuum pressure actuatable arrangement in addition to the user potential actuation aspect thereof. In other words, with an appropriate spring constant for spring 56, a predetermined negative or vacuum pressure within piston 14 can cause valve element 48 to be drawn towards piston closed end 38, thereby compressing spring 56 and at least partially automatically releasing vacuum pressure from piston 14 through opening 70 until equilibrium is established between the vacuum pressure and the strength of spring 56. For example, the strength of spring 56 may be selected such that a vacuum pressure of seventeen inches of Hg or below causes vacuum pressure actuation of vacuum release means 46 so that the degree of vacuum pressure is automatically limited (i.e., at least partially released upon reaching a predetermined threshold of vacuum pressure) for the user's safety and comfort. Accordingly, such an arrangement limits the degree of vacuum pressure which can be applied to the user's penis. It will be readily understood that varying the strength of spring 56 (with all other factors i.e., components, remaining the same) correspondingly varies the predetermined vacuum pressure level at which said vacuum release means is so actuated.

Figures 9, 10:
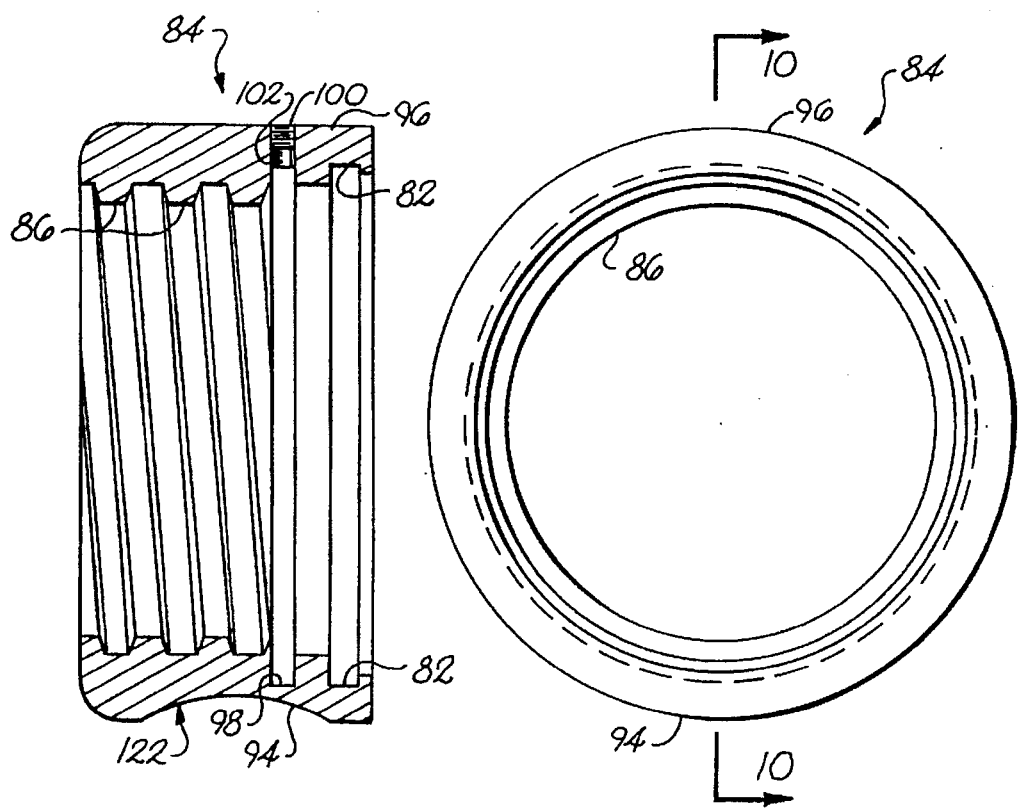
FIG. 9 is an end elevational view of an annular collar in accordance with the subject invention.
FIG. 10 is a cross-sectional view of the exemplary annular collar of present FIG. 9, taken along the sectional line 10—10 indicated therein.

FIGS. 9 and 10 represent end elevational and generally side cross-sectional views, respectively, of rotatable drive collar means generally 84 in accordance with the subject invention and forming part of rotatable drive means 16. Drive coupling means in combination therewith (i.e., in combination with the rotatable drive collar means generally 84) comprise the rotatable drive means generally 16 in accordance with this invention. With collective reference primarily to FIGS. 1 through 6, 9, and 10, rotatable drive means generally 16 are further described as follows.

Rotatable drive collar means 84 are generally received about the vacuum chamber drive region generally 36. Such collar means 84 may be rotated by a user relative to drive region 36, as generally discussed above with reference to arrow 32. In fact, the existence of first threads generally 34 over a longitudinal area of chamber 12 is what defines the drive region 36 of such chamber 12. The rotatable drive means 84 includes matching second threads or inside diameter female threads generally 86 for user controlled threaded operative interaction with the vacuum chamber outside diameter male threads or first threads 34. With such an arrangement, the rotatable drive means 16 are variably longitudinally positioned relative to the vacuum chamber 12 upon selected actuation of such drive means 16. In other words, collar means 84 are selectively positioned along the vacuum chamber drive region 36 by user selected rotation of such collar means 84 relative to drive region 36.

The above is further accomplished by providing a generally longitudinal guide slot generally 88 in drive region 36 of vacuum chamber 12. Drive coupling means generally 90 are associated with such vacuum chamber drive region generally longitudinal guide slot 88 and operatively interconnect the rotatable drive collar means generally 84 with piston generally 14 such that user selected positioning of such collar means 84 establishes corresponding movement and positioning of piston 14 relative to vacuum chamber 12. With such an arrangement, a user selectively controls vacuum engorgement of the user's penis received in vacuum chamber 12 simply by selectively rotating the rotatable drive collar means generally 84. In actual practice for given patients, achieving such engorgement may involve fairly progressive outward movement of piston 14, or may involve relatively staged movement of piston 14 with waiting periods at each stage, all as subjectively determined by a user.

As further variously shown in the figures, such drive coupling means generally 90 may include a coupling pin 92 extending from opposing sidewalls 94 and 96 of collar means 84. Such collar means includes an inside diameter annular channel 98 into which coupling pin 92 may be movably received. Such collar means 84 further includes a closable opening 100 through the sidewall 96 thereof and through which coupling pin 92 may be introduced into annular channel 98. A set screw 102 or the like may be utilized for selectively closing opening 100.

As otherwise variously shown throughout the figures (see especially FIG. A), longitudinal slot 88 preferably extends through opposing sidewalls 104 and 106 of vacuum chamber 12 so as to longitudinally bisect such vacuum chamber 12 in drive region 36 thereof. Thereafter, the coupling pin 92 may extend from the opposing sidewalls 94 and 96 of collar means 84, through the vacuum chamber longitudinal slot 88, in to a coupling arrangement with piston 14. Such coupling arrangement may include connected passage through openings 108 and 110 formed adjacent to end 38 of piston 14 (see FIGS. 5 and 6). It will be understood that during operations coupling pin 92 in fact travels longitudinally in slot 88 while collar means 84 rotates about pin 92 with pin 92 captured within annular channel 98.

It is preferred that at least a portion of the vacuum chamber 12 be comprised of optically transparent material, for example, a plastic, such as Lexan. With such an arrangement, a user may readily observe the changing conditions of the male sex organ and manipulate either the rotatable drive means generally 16 or vacuum release means 46 accordingly.

It will be likewise expected that those of ordinary skill in the art may variously practice additional features in combination with the subject invention, such as represented by present FIGS. 1 and 11 through 13. Present FIG. 11 illustrates a side elevational view (in partial cutaway) of an optional extension 22 which may be fitted over generally end 20 of vacuum chamber 12. As represented in FIG. 1 especially, such end 20 has a reduced outside diameter region generally 112 which is matched by an annular stop region 114 of exemplary extension 22. Such arrangement permits extension 22 to be firmly fitted onto vacuum chamber 12.

It will be understood by those of ordinary skill in the art that such extension 22 may serve various purposes. For example, one exemplary embodiment of the subject invention may have a vacuum chamber of approximately 2.25 inches in the inside diameter thereof, generally 116, with an overall length of about 11 inches. An extension element of several additional inches may be provided through use of element 22. Alternatively, a pre-stretched cincture ring may be carried on the outside diameter, generally 118 of extension element 22 so as to be controllably and selectively received on to the base of the user's penis upon obtaining a desired level of engorgement in accordance with the subject invention. Such a cincture device may be placed over region 112 of chamber 12 if an extension such as 22 is not used.

Still further, FIGS. 12 and 13 represent end and side elevational views respectively of an insert 24 with a shoulder or stop 119 which may be sized for alternatively fitting with an end generally 120 of extension insert 22 or for fitting into end 20 of chamber 12. In some embodiments, the purpose of such insert 24 may be for providing a rubberized or similar material cushion to permit the application of a relative amount of force as end 20 (or extension 22) is pressed against the user's torso during practice of the subject invention.

It will be recognized that still further features may be included and/or practiced without departing from the spirit of the invention. For example, an additional valve may be included for providing a safety limit to the level of negative pressure which can be achieved by the vacuum chamber. Such a device would prevent excessive vacuum force for patient safety. Of course, a user could otherwise release vacuum force with other features described above, or could simply reverse rotate collar means 84 to relieve vacuum force.

Those of ordinary skill in the art will appreciate both from the discussion herewith and the figures themselves, additional aspects of the present invention which may be practiced and/or varied with particular embodiments. For example, collar means generally 84 may be provided with a plurality of indentations generally 122 for the purpose of improving the user's grip. Likewise, drive region 36 of vacuum chamber 12 may be provided with a region generally 124 thereof in which the vacuum chamber outside diameter has no threads 34. Such a space facilitates gripping arrangements for a user during practice of the subject invention.

Generally referencing a methodology for improved vacuum generation for augmenting male potency in accordance with the subject invention, it will be understood that a user's male sex organ or penis is received into vacuum chamber 12 via end opening 18 thereof. Thereafter, a user (or assistant or partner of such user) causes actuation of rotatable drive means generally 16 such that the level of resulting vacuum applied to the user's male sex organ is desirably controlled. As will be understood, air displacement will occur by virtue of properly rotating the collar means 84 to cause the end 38 of piston 14 to move away from the user's torso, thereby creating a negative pressure effect within vacuum chamber 12, which has known vacuum engorgement beneficial effects on the user's penis.

By selectively manipulating collar means 84 (and with proper placement of the apparatus), a user may induce penile engorgement to a desired level. Thereafter, a cincture ring or similar device, such as referenced above in conjunction with patent disclosures incorporated herein by reference, may be moved from end 20 or from extension 22 onto and around the root or base of the user's penis for retaining the engorged condition thereof. Subsequently, vacuum release means generally 46 may be actuated so as to release the vacuum pressure within chamber 12 to permit ready withdrawal of the user's penis from such chamber. Through practice of such methodology, and through using the present apparatus, a user thereby achieves a desired engorgement or erect condition of the penis suitable for intercourse.

It will be further appreciated that various modifications and variations may be practiced. For example, different materials, such as various plastics (whether optically transparent or not) may be practiced. Likewise, varying dimensions may be practiced, as well as different arrangements for suitably effecting rotatable drive force from a user actuatable rotating member for selectively moving a drivable piston within a vacuum chamber for producing a desired air displacement for vacuum generating apparatus for augmenting male potency. In such context, it should be further understood by those of ordinary skill in the art that the foregoing presently preferred embodiments (both apparatus and methodology) are exemplary only, and that the attendant description thereof is likewise by way of words of example rather than words of limitation, and their use does not preclude inclusion of such modifications, variations, and/or additions to the present invention as would be readily apparent to one of ordinary skill in the art, the scope of the present invention being set forth in the appended claims.

What is claimed is:

1. A vacuum generating apparatus for augmenting male potency, comprising:

a vacuum chamber with at least one end adapted for receiving a user's male sex organ;

a drivable piston movably received in said vacuum chamber such that controlled movement thereof away from said at least one end of said vacuum chamber at least partially displaces air within said vacuum chamber so as to generate a corresponding level of vacuum in said vacuum chamber; and rotatable drive means, responsive to user selected rotation thereof, for controllably moving said drivable piston so that a user controls the level of resulting vacuum applied with said apparatus to the user's male sex organ.

2. A vacuum generating apparatus as in claim 1, wherein:

said vacuum chamber is generally cylindrical; and said piston is generally cylindrical with a relatively smaller diameter than that of said vacuum chamber so as to be received therein, said piston including at least one closed end such that its movement in said vacuum chamber relatively sweeps air through said vacuum chamber for air displacement.

3. A vacuum generating apparatus as in claim 2, wherein said piston further includes a generally hollow tubular portion for at least partially projecting around a user's male sex organ received in said vacuum chamber.

4. A vacuum generating apparatus as in claim 3, further including an O-ring seal situated between said hollow tubular portion of said piston and said vacuum chamber.

5. A vacuum generating apparatus as in claim 2, further including vacuum release means for regulating the release of vacuum from said vacuum chamber.

6. A vacuum generating apparatus as in claim 5, wherein said vacuum release means comprises an actuatable vacuum pressure release valve seated in said closed end of said piston so as to permit the selective release of vacuum therethrough.

7. A vacuum generating apparatus as in claim 6, wherein said vacuum release means includes a vacuum pressure actuator for automatically actuating said vacuum pressure release valve upon reaching a predetermined vacuum chamber vacuum pressure, for user safety and comfort.

8. A vacuum generating apparatus as in claim 2, wherein said vacuum chamber includes first threads on at least a longitudinal portion thereof, and said rotatable drive means includes matching second threads engaged with said first threads so that said rotatable drive means is variably longitudinally positioned relative to said vacuum chamber upon selected actuation of said rotatable drive means.

9. A vacuum generating apparatus as in claim 8, wherein:

said vacuum chamber includes an inside diameter, a sidewall, and an outside diameter;

said first threads comprise male threads formed on said outside diameter of said vacuum chamber in a defined drive region thereof;

said vacuum chamber further includes a longitudinal slot formed through said sidewall thereof in said drive region thereof;

said rotatable drive means includes a generally annular collar received about said vacuum chamber, and further includes a coupling member extendable through said vacuum chamber longitudinal slot and interconnecting said annular collar with said drivable piston for controlled movement of said collar; and further wherein said second threads comprise female threads formed on said inside diameter of said annular collar.

10. A vacuum generating apparatus as in claim 9, wherein:

at least a portion of said vacuum chamber comprises optically transparent material; and wherein said apparatus further includes seal means operative between said piston and said vacuum chamber for facilitating the generation of a vacuum in said vacuum chamber;

an actuatable vacuum pressure release valve seated in said piston closed end so as to permit the selective release of vacuum therethrough;

a valve actuation member carried on said collar and operatively interconnected with said vacuum pressure release valve for user actuation thereof; and a vacuum pressure actuator operative with said vacuum pressure release valve for actuation thereof upon generation of a predetermined maximum allowable vacuum in said vacuum chamber.

11. A vacuum generating system for therapeutically producing vacuum engorgement of a user's penis, said system comprising:

an elongated, generally cylindrical configuration vacuum chamber of sufficient size to cover a user's penis, said chamber including an opening in at least one longitudinal end thereof for receiving the user's penis whenever said at least one end is pressed against the user's lower torso, and further including an outside diameter with male threads, defining a drive region of said vacuum chamber, and accompanied by a generally longitudinal guide slot in such drive region;

a piston with at least one closed end movably received in said vacuum chamber, and seal means operative therewith for permitting air displacement within said vacuum chamber whenever said piston is moved away from said at least one end of said vacuum chamber with said vacuum chamber at least one end pressed against the user's lower torso while the user's penis is received within said vacuum chamber;

rotatable drive collar means, generally received about said vacuum chamber drive region and user rotatable relative thereto, and having inside diameter female threads formed therein for user controlled threaded operative interaction with said vacuum chamber outside diameter male threads, such that said collar means is selectively positioned along said vacuum chamber drive region by user selected rotation of said collar means relative to said vacuum chamber drive region;

drive coupling means, associated with said generally longitudinal guide slot of said vacuum chamber drive region and operatively interconnecting said rotatable drive collar means with said piston such that user selected positioning of said collar means establishes corresponding movement and positioning of said piston relative to said vacuum chamber, such that a user selectively controls vacuum engorgement of the user's penis received in said vacuum chamber by selectively rotating said rotatable drive collar means; and vacuum release means subject to actuation for controllably admitting air into said vacuum chamber so as to release vacuum pressure in said vacuum chamber for withdrawal of the user's penis from said vacuum chamber.

12. A vacuum generating system as in claim 11, wherein:

at least a portion of said vacuum chamber is optically transparent so as to permit observation of the user's penis during vacuum engorgement thereof;

said piston includes a tubular sleeve extending from said at least one closed end thereof towards said at least one longitudinal end of said vacuum chamber, and adapted to project around a user's penis received in said vacuum chamber; and said seal means comprises an O-ring received between said vacuum chamber and said tubular sleeve of said piston.

13. A vacuum generating system as in claim 11, wherein:

said longitudinal guide slot of said vacuum chamber drive region extends through opposing sidewalls of said vacuum chamber so as to longitudinally bisect said vacuum chamber in said drive region thereof; and said drive coupling means includes a coupling pin extending from opposing sidewalls of said collar means, through said longitudinal guide slot of said vacuum chamber drive region, and coupling with said piston.

14. A vacuum generating system as in claim 13, wherein:

said collar means includes an inside diameter annular channel into which said coupling pin is movably received, and further includes a sidewall defining a closable opening through which said coupling pin may be introduced into said annular channel; and said coupling pin is received through said piston relatively adjacent said at least one closed end thereof.

15. A vacuum generating system as in claim 11, wherein said vacuum release means includes an actuatable vacuum pressure release valve seated in said piston closed end, a valve actuation member carried on said collar means and operatively interconnected with said vacuum pressure release valve for user actuation thereof, and a vacuum pressure actuator for automatically actuating said vacuum pressure release valve upon reaching a predetermined vacuum chamber vacuum pressure.

16. Vacuum generating methodology for augmenting male potency, comprising:

providing a vacuum chamber with at least one end adapted for receiving a user's male sex organ;

movably providing a drivable piston in said vacuum chamber such that controlled movement thereof away from said at least one end of said vacuum chamber at least partially displaces air within said vacuum chamber so as to generate a corresponding level of vacuum in said vacuum chamber;

establishing rotatable drive means, responsive to user selected rotation thereof, for controllably moving said drivable piston; and receiving a user's male sex organ in said vacuum chamber with the user thereafter causing actuation of said rotatable drive means such that the user controls the level of resulting vacuum applied to the user's male sex organ.

17. A vacuum generating methodology as in claim 16, wherein:

said steps of establishing said rotatable drive means and providing said vacuum chamber further include providing threading on said rotatable drive means and said vacuum chamber operatively associated with each other for causing movement of said piston; and said method further includes the step of rotating said drive means relative to said vacuum chamber for actuation of said rotatable means.

18. A vacuum generating methodology as in claim 17, further including:

providing user controllable vacuum release means for regulating the release of vacuum from said vacuum chamber; and actuating said vacuum release means after obtaining a desired erection of the user's male sex organ through operation of said vacuum chamber.

19. A vacuum generating methodology as in claim 18, further including using a cincture ring for capturing an erection of the male sex organ prior to actuating said vacuum release means.

20. A vacuum generating methodology as in claim 19, further including providing a vacuum pressure actuator responsive to a predetermined vacuum chamber vacuum for automatically actuating said vacuum release means so as to limit the vacuum applied to the user's male sex organ, for user safety and comfort.

21. A vacuum generating method for therapeutically producing vacuum engorgement of a user's penis, said method comprising:

providing an elongated, generally cylindrical configuration vacuum chamber of sufficient size to cover a user's penis, said chamber including an opening in at least one longitudinal end thereof for receiving the user's penis with said at least one end pressed against the user's lower torso, and further including an outside diameter with male threads, defining a drive region of said vacuum chamber, and accompanied by a generally longitudinal guide slot in such drive region;

providing a piston with at least one closed end movably received in said vacuum chamber, and seal means operative therewith for permitting air displacement within said vacuum chamber whenever said piston is moved away from said at least one end of said vacuum chamber with said vacuum chamber at least one end pressed against the user's lower torso while the user's penis is received within said vacuum chamber;

providing rotatable drive collar means, generally received about said vacuum chamber drive region and user rotatable relative thereto, and having inside diameter female threads formed therein for user controlled threaded operative interaction with said vacuum chamber outside diameter male threads, such that said collar means is selectively positioned along said vacuum chamber drive region by user selected rotation of said collar means relative to said vacuum chamber drive region;

providing drive coupling means, associated with said vacuum chamber drive region generally longitudinal guide slot and operatively interconnecting said rotatable drive collar means with said piston such that user selected positioning of said collar means establishes corresponding movement and positioning of said piston relative to said vacuum chamber;

providing vacuum release means subject to user actuation for controllably admitting air into said vacuum chamber so as to release vacuum pressure therein;

placing a user's penis into said vacuum chamber through said at least one longitudinal end opening thereof with said at least one end pressed against the user's lower torso;

actuating said rotatable drive collar means such that a user selectively controls vacuum engorgement of the user's penis received in said vacuum chamber by selectively rotating said rotatable drive collar means; and actuating said vacuum release means so as to release vacuum pressure in said vacuum chamber for withdrawal of the user's penis therefrom, after achieving desired vacuum engorgement of the user's penis.

22. A vacuum generating method as in claim 21, further including providing at least part of said vacuum chamber comprised of optically transparent material so as to permit observation of the user's penis during vacuum engorgement thereof.

23. A vacuum generating method as in claim 21, further including using a cincture ring for capturing a desired engorged condition of the user's penis prior to actuating said vacuum release means.

24. A vacuum generating method as in claim 21, further including providing a vacuum limiter for automatically actuating said vacuum release means upon reaching a predetermined vacuum chamber vacuum pressure, for user safety and comfort.

\* \* \* \* \*